United States Patent
Ikeda et al.

(10) Patent No.: US 10,098,875 B2
(45) Date of Patent: *Oct. 16, 2018

(54) METHOD OF TREATMENT FOR MENTAL DISORDERS

(71) Applicant: Sumitomo Dainippon Pharma Co., Ltd., Osaka-shi, Osaka (JP)

(72) Inventors: Kazuhito Ikeda, Osaka (JP); Takeo Ishiyama, Osaka (JP)

(73) Assignee: SUMITOMO DAINIPPON PHARMA CO., LTD., Osaka-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/995,044

(22) Filed: Jan. 13, 2016

(65) Prior Publication Data

US 2016/0129000 A1 May 12, 2016

Related U.S. Application Data

(60) Division of application No. 13/555,044, filed on Jul. 20, 2012, now Pat. No. 9,259,423, which is a continuation of application No. 13/113,703, filed on May 23, 2011, now Pat. No. 8,258,139.

(60) Provisional application No. 61/411,081, filed on Nov. 8, 2010.

(30) Foreign Application Priority Data

Feb. 18, 2011 (JP) ................................ 2011-033453

(51) Int. Cl.

| A61K 31/428 | (2006.01) |
|---|---|
| A61K 31/496 | (2006.01) |
| A61K 31/4035 | (2006.01) |
| A61K 45/06 | (2006.01) |
| A61K 9/00 | (2006.01) |
| A61K 9/20 | (2006.01) |

(52) U.S. Cl.
CPC .......... *A61K 31/496* (2013.01); *A61K 9/0053* (2013.01); *A61K 9/20* (2013.01); *A61K 45/06* (2013.01); *A61K 31/4035* (2013.01); *A61K 31/428* (2013.01)

(58) Field of Classification Search
CPC . A61K 31/428; A61K 31/496; A61K 31/4035
See application file for complete search history.

(56) References Cited

U.S. PATENT DOCUMENTS

| 5,444,073 A | 8/1995 | Perregaard et al. |
|---|---|---|
| 5,532,372 A | 7/1996 | Saji et al. |
| 5,780,632 A | 7/1998 | Saji et al. |
| 6,964,962 B2 | 11/2005 | Wong et al. |
| 7,067,507 B2 | 6/2006 | Pulley et al. |
| 2003/0050307 A1 | 3/2003 | Ruhland et al. |
| 2006/0025422 A1 | 2/2006 | Nakamura et al. |
| 2006/0111429 A1 | 5/2006 | Fish et al. |
| 2006/0142276 A1 | 6/2006 | Ohno et al. |
| 2008/0255148 A1 | 10/2008 | Ohno et al. |
| 2009/0176800 A1 | 7/2009 | Ishiyama |
| 2010/0105692 A1 | 4/2010 | Moheno et al. |

FOREIGN PATENT DOCUMENTS

| EP | 0 464 846 A1 | 1/1992 |
|---|---|---|
| JP | 05-17440 A | 1/1993 |
| JP | 6-504787 A | 6/1994 |
| JP | 08-333368 | 12/1996 |
| JP | 11-500745 | 1/1999 |
| JP | 2000-281576 | 10/2000 |
| JP | 2008-135074 A | 5/2003 |
| JP | 2003-160583 | 6/2003 |
| JP | 2003-519226 A | 6/2003 |
| WO | WO 93/16073 | 8/1993 |
| WO | WO 95/34306 | 12/1995 |
| WO | WO 96/14297 | 5/1996 |
| WO | WO 97/13759 | 4/1999 |
| WO | WO 99/52519 | 10/1999 |
| WO | WO 02/24166 A1 | 3/2002 |
| WO | WO 2002/22581 A1 | 3/2002 |
| WO | WO 2003/066039 A1 | 8/2003 |
| WO | WO 2004/017973 | 3/2004 |
| WO | WO 2004/113333 | 12/2004 |
| WO | WO 2007/124757 A2 | 11/2007 |
| WO | WO 2008/124030 | 10/2008 |

OTHER PUBLICATIONS

Office Action dated Dec. 15, 2016 in U.S. Appl. No. 14/994,939, filed Jan. 13, 2016.
"Delirium, Dementia, Amensia, Cognitive Disorders," http://www.nlm.nih.gov/cgi/mesh/2009/MB_cgi?mode=&term...m,+Dementia,+Amnestic,+Cognitive+Disorders&Disorders&field=entry, accessed Jul. 1, 2009.
Alphs, Larry, "An industry perspective on the NIMH Consensus Statement on negative symptoms," Schizophrenia Bulletin, vol. 32, No. 2, pp. 225-230, (2006).
Approval Labeling Text, NDA 21-487, NAMENDA™ (memantine hydrochloride) (2003).
Australian Guidelines on ADHD, Jun. 2009, pp. 1-291.

(Continued)

*Primary Examiner* — Samira J Jean-Louis
(74) *Attorney, Agent, or Firm* — Oblon, McClelland, Maier & Neustadt, L.L.P.

(57) ABSTRACT

The invention relates to a medicament or a method for treating mental disorders, in detail, ADHD comprising lurasidone, or a combination of lurasidone and a $D_4$ receptor agonist.

8 Claims, 8 Drawing Sheets

(56) References Cited

OTHER PUBLICATIONS

Barber, Teresa A., et al., "Memantine ameliorates scopolamine-induced amnesia in chicks trained on taste-avoidance learning," Neurobiology of Learning and Memory vol. 93, pp. 540-545, (2010).
Bejar, Corina, et al., "Effect of rivastigmine on scopolamine-induced memory implairment in rats," European Journal of Pharmacology, vol. 383, pp. 231-240, (1999).
Biederman, Joseph, et al., "Risperidone treatment for ADHD in children and adolescents with bipolar disorder," Neuropsychiatric Diseases and Treatment, vol. 4, No. 1, pp. 203-207 (2008).
Botero, Hector M. et al., "Structure—Activity Relationships in a Series of Bisquaternary Bisphthalimidine Derivatives Modulating the Muscarinic M2-Receptor Allosterically," J. Med. Chem., vol. 43, pp. 2155-2164, (2000).
Bowen, D.M., "Traditional pharmacotherapy may succeed in alzheimer's disease," Trends in Neurosciences, vol. 15, No. 3, pp. 84-85, (1992).
Bruno, et al, The α2c-adrenergic receptor mediates hyperactivity of colobomo mice, a model of attention deficit hyperactivity disorder, Neurobiology of Disease, vol. 23, pp. 679-688, (2006).
Center for Drug Evaluation and Research, Pharmacology Reviews at FDA, pp. 1-260, (Oct. 2010).
Clinton et al., Altered transcript expression of NMDA, receptor associated postsynaptic proteins in the thalamus of subject with schizohrenia, Am. J. Psychiatry, vol. 160, No. 6, pp. 1100-1109, (Jun. 2003).
Clinton et al., "Thalamic expression of NMDA receptor-associated postsynaptic density proteins in schizophrenia," Society for Neuroscience, Program No. 754.4, (2003), (online) (abstract only).
Cloninger, "The discovery of susceptibility genes for mental disorders," Proc. Natl. Acad. Sci. vol. 99, No. 21, pp. 13365-13367, (Oct. 15, 2002).
Corbett, "Clozapine but not haloperidol antagonizes an MK-801 discriminative stimulus cue," Pharmacol. Biochem. Behav., vol. 51(2-3), pp. 561-564, (1995).
Diagnostic and Statistical Manual of Mental Disorders, Fourth Edition (DSM-IV™) pp. 273-278, 285, and 286 (1994), published by the American Psychiatric Association, Washington D.C.
Didriksen, et al., "Antipsycholtic of the Gly T-1 inhibitor NFPS," Society Neuroscience Abstract, vol. 2002, abstract No. 893.1, (2002).
Doggrell, Sheila A. et al., "Treatment of dementia with neurotransmission modulation," Expert Opinion on Investigational Drugs, vol. 12, No. 10, pp. 1633-1654, (2003).
Duka, Theodora, "Scopolamine-induced amnesia in humans: Lack of effects of the benzodiazepine receptor antagonist β-carboline ZK 93426," Journal of Psychopharmacology, vol. 6, No. 3, pp. 382-388, Abstract, (1992).
Ebihara, Mitsuru et al., "Togo Scicchosho no Dobutsu Model," Igaku no Ayumi, vol. 208, No. 3, pp. 138-142, (2004).
Emre, Murat, M.D. et al., "Rivastigmine for dementia associated with parkinson's disease," The New England Journal of Medicine, vol. 351, No. 24, pp. 2509-2518, (2004).
English translation of Office Action from the Chinese Patent Office in Appln. No. 200480017534.X dated Jan. 29, 2010.
English translation of Office Action from the Japanese Patent Office in Appln. No. 2005-507314 dated Jun. 29, 2010.
English translation of Second Office Action from the Chinese Patent Office in Appln. No. 200480017534.X dated Jan. 29, 2010.
Enomoto et al., "Development of antipsychotics by using animal model," Brain Science, vol. 25, No. 5, pp. 437-444 (2003).
EP Official Action for Corresponding EP Application No. 04 746 564.6-2117 dated Aug. 27, 2010.
EP Official Action for Corresponding EP Application No. 04 746 564.6-2117 dated Nov. 20, 2009.
EP Search Report for European Patent Application No. 04746564.6 dated Mar. 2, 2009.
EP Search Report for European Patent Application No. 11160001.1-2123 dated Jul. 19, 2011.
Erhart, Stephen M., et al., "Treatment of schizophrenia negative symptoms: future prospects," Schizophrenia Bulletin, vol. 32, No. 2, pp. 234-237, 2006.
European Neuropsychopharmacology, "P.3.155 Efficacy of lurasidone (SM-13496) in the treatment of schizophrenia: results of two, phase 2, pacebo-controlled studies," vol. 15, pp. S522-S523, (2005).
European Patent Office Communication, dated Feb. 6, 2014, with Supplemental European Search Report for EP Application No. 11840252.8.
Fabre, Serge et al., "Protein Kinase C Inhibitors; Structure—Activity Relationships in K252c-Related Compounds," Bioorg. Med. Chem. vol. 1, No. 3, pp. 193-196, (1993).
Fernandez, Hubert H. et al., "Pharmacotherapy of dementia with Lewy bodies," Expert Opinion on Pharmacotherapy, vol. 4, No. 11, pp. 2027-2037, (2003).
Final Office Action in U.S. Appl. No. 10/525,021 dated Mar. 5, 2010.
Final Office Action in U.S. Appl. No. 10/525,021 dated Sep. 17, 2008.
Final Office Action in U.S. Appl. No. 12/140,927 dated Jul. 10, 2009.
Final Office Action in U.S. Appl. No. 12/140,927 dated Jul. 18, 2011.
Final Office Action in U.S. Appl. No. 12/401,958 dated Apr. 5, 2010.
Friedman, Joseph I., "Cholinergic targets for cognitive enhancement in schizophrenia: focus on cholinesterase inhibitors and muscarinic agonists," Psychopharmacology, 174, pp. 45-53, (2004).
Geyer et al., "Animal behavior models of the mechanisms underlying antipsychotic atypicality," Progress in Neuro-Psychopharmacology & Biological Psychiatry, vol. 27, pp. 1071-1079, (2003).
Goff et al., "The emerging role of glutamate in the pathophysiology and treatment of schizophrenia," Am. J. Psychiatry, vol. 158, No. 9, pp. 1367-1377, (Sep. 2001).
Harrod et al., "MK-801 induced retrieval, but not acquisition, deficits for passive avoidance conditioning," Pharmacology, Biochemistry, and Behavior, vol. 69, pp. 585-593, (2001).
Harvey et al., "Cognition in schizophrenia: from basic science to clinical treatment" Psychopharmacology, vol. 169, pp. 213-214, (2003).
Harvey et al., "Cognitive functioning in schizophrenia: a consensus statement on its role in the definition and evaluation of effective treatments for the illness," J. Clin. Psychiatry, vol. 65, pp. 361-372, (2004).
Hyman et al., "What are the right targets for psychopharmacology?" Science, vol. 299, pp. 350-351, (Jan. 17, 2003).
Ibrahim et al., "Ionotropic glutamate receptor binding and subunit mRNA expression in thalmic nuclei in schizophrenia," Am. J. Psychiatry, vol. 159, No. 11, pp. 1811-1623, (Nov. 2000).
International Preliminary Report on Patentability for International Application No. PCT/JP2011/062314 dated May 23, 2013.
International Search Report for International Application No. PCT/JP2004/009095 dated Aug. 24, 2004.
International Search Report for International Application No. PCT/JP2011/062314 dated Jun. 28, 2011.
Ishibashi, Tadashi et al., "Pharmacological Profile of Lurasidone, a Novel Antipsychotic Agent with Potent 5-Hydroxytryptamine 7 (5-HT$_7$)and 5-HT$_{1A}$ Receptor Activity," Journal of Pharmacology and Experiemental Therapeutics, Published online Apr. 2010, vol. 334, No. 1, pp. 171-181.
Ishiyama, T., et al., "Effects on sm-13496, a novel serotonin-dopamine antagonist, and other antipsychotics on cognitive performance in rat passive avoidance test," abstract, vol. 23, (2003).
Ishizumi, Kikuo, et al., "Succinimide Derivatives. II. Synthesis and Antipsychotic Activity of N-[4-[4-(1,2-Benzisothiazol-3-yl)-1-piperazinyl]butyl]-1,2-cis-cyclohexanedicarboximade (SM-9018) and Related Compounds," Chem. Pharm. Bull., vol. 43, No. 12,pp. 2139-2151, (1995).
Japanese Office Action in corresponding Japanesse Application No. 2006-510283 dated May 31, 2011.

(56) References Cited

OTHER PUBLICATIONS

Jellinger, Kurt A., "The Pathology of Ischemic-Vascular Dementia: An Update," Journal of the Neurological Sciences 203-204, pp. 153-157, (2002).
Kahle, Philipp J. et al., "The Emerging Utility of Animal Models of Chronic Neurodegenerative Diseases," Emerging Therapeutic Targets, vol. 5, No. 1, 125-132, (2001).
Kane, John, "Commentary: Consensus statement on negative symptoms," Schizophrenia Bulletin, vol. 32, No. 2, pp. 223-224, (2006).
Kasper et al., "Cognitive effects and antipsychotic treatment," Psychoneuroendocrinology, vol. 28, pp. 27-38, (2003).
Kay, Stanley R. et al, "The Positive and Negative Syndrome Scale (PANSS) for Schizophrenia." Schizophrenia Bulletin. vol. 13, No. 2, pp. 261-276, (1987).
Kirkpatrick, Brian, et al., "The NIMH-MATRICS consensus statement on negative symptoms," vol. 32, No. 2, pp. 214-219, (2006).
Krystal et al., "NMDA receptor antagonist effects, cortical glutamatergic function, and schizophrenia: toward a paradign shift in medication development," Psychopharmacology, vol. 169, pp. 215-233, (2003).
Laughren, Thomas, et al., "Food and Drug Administration perspective on negative symptoms in schizophrenia as a target for a drug treatment claim," Schizophrenia Bulletin, vol. 32, No. pp. 220-222, (2006).
Lindenmayer et al., "A new five factor model of schizophrenia," Psychiatric Quarterly, vol. 65, No. 4. pp. 299-322, (1994).
Malenka et al., "Long term potentiation—A decade of process?" Science, vol. 285, pp. 1870-1874, (Sep. 17, 1999).
Masi, Gabriele, et al., "Aripiprazoie monotherapy in children and young adolescents with perfasive development disorders," CNS Drugs, vol. 23, No. 6, pp. 511-521, (2009).
Meitzer et al., "Cognition, schizophrenia, and the atypical antipsychotic drugs," Proc. Natl. Acad. Sci., vol. 96, No. 24, pp. 13591-13593, (Nov. 23, 1999).
Mettey Y, et al., "Synthesis of 11-Aminodibenzol[b,f][1,4]thiazepines and Fluoro Derivatives," Journal of Heterocyclic Chemistry, vol. 03-04 No. 34, pp. 465-467, (1997).
Meyer, Jonathan, M. et al., "Lurasidone: a new drug in development for schizophrenia," Expert Opinion on Investigational Drugs, vol. 18, No. 11, pp. 1715-1726, (2009).
Misane et al., "Selective 5-HTIA Antagonists WAY 10065 and NAD-299 Attenuate the Impairment of Passive Avoidance Caused by Scopolamine in the Rat," Neuropsychopharmacology 28, pp. 253-264, (2003).
Miyachi, Hiroyuki et al., "Novel Biological Response Modifiers: Phthalimides with Tumor Necrosis Factor-α Production-Regulating Activity," J. Med. Chem.,vol. 40, pp. 2858-2865, (1997).
Miyamoto et al., "Hyperfunction of dopaminergic and serotonergic neuronal systems in mice lacking the NMDA receptor E1 subunit," Journal of Neuroscience, vol. 21, No. 2, pp. 750-757, (Jan. 15, 2001).
Moghaddam, "Bringing order to the glutamate chaos in schizophrenia," Neuron, vol. 40, pp. 881-884, (Dec. 4, 2003).
Mohn et al., ., "Mice with reduced NMDA receptor expression display behaviors related to schizophrenia," Cell, vol. 98, pp. 427-436, (1999).
Myhrer, "Neurotransmitter systems involved in learning and memory in the rat: a meta-analysis based on studies of four behavioral tasks," Brain Research Reviews, vol. 41, pp. 268-287, (2003).
Nakagawa et al., "Ethanol-induced state-dependent learning is mediated by 5-hydroxytryptamine3 receptors but not by N-methyl-D-aspartate receptor cornplex," Brain Research, vol. 706, pp. 227-232, (1996).
Newman-Tancredi et al., Agonist and antagonist properties of antipsychotics at human $D_{4.4}$ receptors: G-protein activation and $K^+$ channel modulation in transfected cells, J. Int. of Neuropsychopharmacology, vol. 11, Iss. 3, abstract.
Nippon-Shinkei-Seishin-Yakurigaku Zasshi (JPn, J. Neuropsychopharmacol.) 23: 296 (2003).
Noda et al, "Ciozapine, but not haloperidol, reverses working memory impairment induced by chronic PCP administration in rats: a new model for cognitive dysfunction in schizophrenia," Abstracts Society Neuroscience, vol. 26, Nos. 1-2, pp. 6533, (2000).
Norman, Mark H. et al., "Effect of Linking Bridge Modifications on the Antipsychotic Profile of Some Phthalimide and Isoindolinone Derivatives," Journal of Medical Chemistry, vol. 39, No. 1, pp. 149-157, (1996).
Notice of Allowance and Fees Due in U.S. Appl. No. 12/140,927, dated Dec. 1, 2011.
Office Action in Japanese Application No. 2005-507314 dated Jun. 29, 2010 (4 pages).
Office Action in U.S. Appl. No. 10/525,021 dated Aug. 29, 2007.
Office Action in U.S. Appl. No. 10/525,021 dated Dec. 17, 2007.
Office Action in U.S. Appl. No. 10/525,021 dated Jun. 12, 2009.
Office Action in U.S. Appl. No. 10/562,039 dated Mar. 18, 2008.
Office Action in U.S. Appl. No. 10/589,804 dated Dec. 11, 2008.
Office Action in U.S. Appl. No. 12/140,927 (continuation of U.S. Appl. No. 10/562,039) dated Oct. 3, 2008.
Office Action in U.S. Appl. No. 12/140,927 dated Nov. 10, 2010.
Office Action in U.S. Appl. No. 12/401,958 (continuation of U.S. Appl. No. 10/589,804) dated Oct. 1, 2009.
Ogasa et al., "SM-13496 in patients with acute exacerbation of schizophrenia: A two-dose double-blind phase II comparison with placebo", Schizophrenia Research, vol. 60, No. 1, pp. 297, (2003).
Oshimo Takashi, Prog. Med. 2009, vol. 29, pp. 1347-1352.
Parnetti, et al., "Cholinergic precursors in the treatment of cognitive impairment of vascular origin: lneffective approaches or need for re-evaluation?," Journal of the Neurological Sciences, vol. 257, pp. 264-269, (2007).
Perricone v. Medicis Pharr. Corp 432 F.3d 1368 (Fed. Cir. 2005).
Perry, Elaine et al., "Acetylcholine in Mind: a Neurotransmitter Correlate of Consciousness?." TINS, vol. 22, No, 6, pp. 273-280 (1999).
Poster exhibited at the 18th European College of Neuropsychopharmacology Congress, Oct. 23-26, 2005.
Powell, Susan, B,, et al., "RO-10-5824 is a selective dopamine D4 receptor agonist that increases novel object exploration in C57 mice," Neuropharmacology, vol. 44, pp. 473-481, (2003).
Prescribing information for "Exelon® (rivastigmine tartrate) Capsules and Oral Solution," (31 pages), (2006).
Prescribing Information for ARICEPT® (donepezil hydrochloride) (14 pages) (2010).
Protais, P. et al., "Climbing behavior induced by apomorphine in mice: a simple test for the study of dopamine receptors in striatum," Psychopharmacology, vol. 50, pp. 1-6, (1976).
Purcell et al., "Common polygenic variation contributes to risk of schizophrenia and bipolar disorder," Nature Letters, 2009. vol. 460, pp. 748-752.
Puttrese, et al., "Localized deletion of the NR1 gene in mouse prefrontal cortex impairs spatial memory," Society Neuroscience Abstract vol. 2003, abstract No. 964.19, (2003).
Reingold, Jennifer L. et al., "Rivastigmine for the Treatment of Dementia Associated with Parkinson's Disease," Neuropsychiatric Disease and Treatment vol. 3, pp. 775-783, (2007).
Roman, Gustavo C. et al., "Donepezil in Vascular Dementia: Combined Analysis of Two Large-Scale Clinical Trials," Dementia and Geriat.. Cogn. Disord., vol. 20 pp. 337-344, (2005).
Romero, Arthur G. et al., "Synthesis of Metabolically Stable Arylpiperazine 5-HT1A Receptor Agonists," Bioorganic & Medicinal Chemistry Letters, vol. 2, No. 12, pp. 1703-1706, (1992).
Russell, Vivienne, A. et al., "Animal models of attention-deficit hyperactivity disorder," Behavioral and Brain Functions, vol. 1, No. 9, pp. 1-17, (2005).
Rutten, K., et al "Selective PDE inhibitors rolipram and sildenafil improve object retrieval performance in adult cynomolgus macaques," Psychopharmacology, vol. 196, pp. 643-648, (2008).
Saito, Kazuhiko et al., Heath and Labor Sciences Research Grant (Clinical Research for Disease of Childhood) 2006, pp. 69-74.
Sharma et al., "Cognitive function in schizophrenia deficits, functional consequences, and future treatment," Psychiatr. Clin. N. Am., vol. 26, pp. 25-40 (2003).
Shinkei Kairomo Keisei to Kofunsei Synapse Kasosei ni Kansura Kodogakuteki Kenkyu pp. 13-12, with partial English language translation, (2003).

(56) References Cited

OTHER PUBLICATIONS

Small, David H., "Acetylcholinesterase Inhibitors for the Treatment of Dementia in Alzheimer's Disease: Do We Need New Inhibitors? ," Expert Opinion on Emerging Drugs, vol. 10, No. 4, pp. 817-823, (2005).
Snyder, Peter J. et al., "Reversal of scopolamine-induced deficits with a single dose of donepezil, an acetylcholinesterase inhibitor," Alzheimer's & Dementia, vol. 1, pp. 126-135, (2005).
Takahashi, Satoshi et al., "Anti-Dementia Drugs and Vascular Dementia," Rinsho-Seishinigaku, (Clinical Psychiatry), vol. 31, No. 10, pp. 1189-1193, (2002).
The Lancet, "The Treatment of Senile Insanity," Lancet Limited, London, GB LNKD-DOI:10.1016/S0140-6736 (01) 05083-8, vol. 208, No. 5381, pp. 820-882, (Oct. 16, 1926).
Thomas, Elizabeth et al., "Specific Impairments in Visuospatial Working and Short-Term Memory Following Los-Dose Scopolamine Challenge in Healthy Older Adults," Neuropsychologia, vol. 46, pp. 2476-2484, (2008).
Tokita, Kenichi et al., "Combination of a Novel Antidementia Drug FK960 with Donepezil Synergistically Improves Memory Deficits in Rats," Pharmacology, Biochemistry and Behavior, vol. 73, pp. 511-519, (2002).
Tokuda, et al, "Effects of SM-13496, an atypical antipsychotic agent, on MK-801-induced learning deficit in rats," J. Pharmacol Sciences, vol. 94, supplement 1, p. 163P, (2004).
Turetsky et al., "Memory-Delineated Subtypes of Schizophrenia: Relationship to Clinical, Neuroanatomical, and Neurophysiological Measures," Neuropsychology, vol. 16, No. 4, pp. 481-490 (2002).
U.S. Appl. No. 10/525,021, filed Feb. 18, 2005.
U.S. Appl. No. 10/562,039, filed Dec. 22, 2005.
U.S. Appl. No. 10/589,804, filed Aug. 17, 2006.
Wang, D., et al. "Synergistic effect of galantamine with risperidone on impairment of social interaction in phencyclidine-treated mice as a schophrenic animal model," Neuropharmacology, vol. 52, pp. 1179-1187 (2007).
Weiss et al., "The effects of second-generation antipsychotics on cognitive functioning and psychosocial outcome in schizophrenia," Psychopharmacology, vol. 162, pp. 11-17, (2002).
Wise, L.E., et al., "Reversal learning in the 8—arm radial maze in rats is impaired by subchronic adminstration of the non-competitive NMDA antagonist ketamine", Society for Neuroscience, abstract, vol. 2002, (2002).
Woolley et al., "Selective dopamine D4 receptor agonist (A-412997) improves cognitive performance and stimulates motor activity without influencing reward-related behaviour in rat," Behavioural Pharmacology, vol. 19, Iss. 8, pp. 765-776, (Dec. 2008).
Xu Taixiang et al, "Status quo and Development of Alzheimer's Disease," Acta Academiae Medicinae Qingdao Universitatis, vol. 37, No. 4, pp. 355-357, (2001).

Haloperidol

Non-parametric Dunnet's test
**:P<0.01

METHOD OF TREATMENT FOR MENTAL DISORDERS

TECHNICAL FIELD

The invention relates to a method for treating mental disorders, in more detail, a novel method for treating ADHD.

BACKGROUND ART

Lurasidone [chemical name: (3aR,4S,7R,7aS)-2-{(1R,2R)-2-[4-(1,2-benzisothiazol-3-yl)piperazin-1-yl-methyl]cyclohexylmethyl}hexahydro-4,7-methano-2H-isoindole-1,3-dione] of the following formula is a compound having a pharmacological activity as an antipsychotic agent, which is characteristic of a high affinity for dopamine $D_2$, serotonin 5-$HT_{1A}$, 5-$HT_{2A}$, 5-$HT_7$, and noradrenaline $\alpha_{2C}$ receptors, and characteristic of minimal to no affinity for histamine $H_1$ and muscarinic $M_1$ receptors. Lurasidone possesses antipsychotic effects, antidepressant- or anxiolytic-like effects, and pharmacological profiles with potentially-reduced liability for extrapyramidal and CNS depressant side effects, which is expected to be used for the treatment of schizophrenia and bipolar disorder (Patent Reference 1, Non-patent Reference 1).

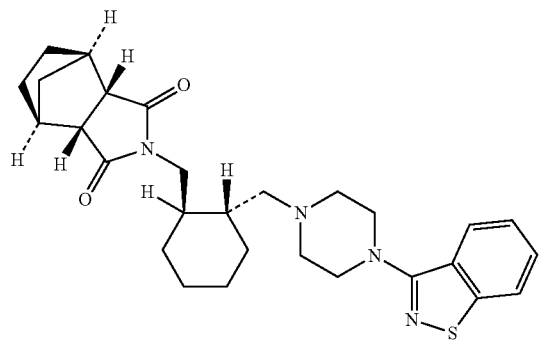 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

Dopamine $D_4$ receptors are one of subtypes of dopamine receptors, which are known as a target in the treatment of schizophrenia or Parkinson's disease.

Attention deficit/hyperactivity disorder (ADHD) is one of developmental disorders, which is characterized by inattention, hyperactivity, and impulsiveness. The symptom includes difficulty in concentrating, overactivity, and inattention. Generally, the symptom is observed in children who are 7 year-old or younger. In addition, the symptom includes inattention-predominant type which is not dominant in overactivity. The incidence rate up to school-age is 1-6%, and the rate of boys is higher than that of girls. ADHD had been thought to be a disease in children and be naturally improved in adults because the cases of hyperactivity decrease with aging. But, currently it is thought that adults can suffer from ADHD.

As a drug therapy for ADHD, central stimulants are used in order to raise patient's arousal level, and methylphenidate hydrochloride is mainly used in America and a sustained preparation of methylphenidate has been approved in Japan as a medicament for treating ADHD in childhood, in addition, atomoxetine hydrochloride which is a noradrenaline reuptake inhibitor is also acceptable in Japan, but the applied patients thereof are limited to children. Thus, there is no medicament therefor for adults in Japan. In America, methylphenidate is acceptable for adults, but, it is indicated that methylphenidate has the same side-effect as psychostimulants such as amphetamine, methamphetamine, and cocaine.

Risperidone, which is one of serotonin/dopamine antagonists (SPDA), has been reported in connection with ADHD (Non-patent Reference 2). However, there has not been any study about the improvement of attention function in ADHD using risperidone.

On the other hand, there is a report about the relationship between dopamine $D_4$ agonist and ADHD (Non-patent References 3 and 4).

PRIOR ART

Patent Reference

[Patent Reference 1] JP 5(1993)-17440 A (U.S. Pat. No. 5,532,372 A)

Non-Patent Reference

[Non-patent Reference 1] Exp Opin Invest Drugs 18(11):
[Non-patent Reference 2] Neuropsychiatric Disease and Treatment 2008: 4(1) 203-207,
[Non-patent Reference 3] Behav Pharmacol. 2008 December; 19(8): 765-76.
[Non-patent Reference 4] Neuropharmacology. 2003 March; 44(4): 473-81.

DISCLOSURE OF INVENTION

Problem to be Solved by the Invention

The purpose of the present invention is to provide a novel medicament for treating ADHD and a novel method therefor. In particular, the purpose is to provide a medicament and a method useful for treating attention function/impulsiveness in ADHD.

Means to Solve the Problem

The present inventors have extensively studied to reach the above object and then has found that lurasidone or a pharmaceutically acceptable acid addition salt thereof of the present invention, as well as a combination of lurasidone or a pharmaceutically acceptable acid addition salt thereof and a $D_4$ receptor agonist of the present invention exhibit the desired therapeutic effect increasing attention function and suppressing impulsiveness caused by ADHD in primates model of ADHD. Based upon the new findings, the present invention has been completed.

One embodiment of the present invention is directed to a method for treating ADHD which comprises administering a therapeutically effective amount of lurasidone or a pharmaceutically acceptable acid addition salt thereof to a mammal in need thereof.

One embodiment of the present invention is directed to the above method wherein treating ADHD is improving attention function in ADHD, i.e. a method for improving attention function in ADHD which comprises administering a therapeutically effective amount of lurasidone or a pharmaceutically acceptable acid addition salt thereof to a mammal in need thereof.

One embodiment of the present invention is directed to the above method which further comprises administering an additional psychotropic drug as a combination drug. The additional psychotropic drug used as a combination drug is preferably a $D_4$ receptor agonist, and the embodiment thereof is a method for treating ADHD which comprises administering a therapeutically effective amount of lurasidone or a pharmaceutically acceptable acid addition salt thereof and a therapeutically effective amount of a $D_4$ receptor agonist to a mammal in need thereof; in particular, the method for improving attention function in ADHD.

The $D_4$ receptor agonist used herein is preferably one or more medicaments selected from the group consisting of PD-168077, ABT-724, ABT-670, F-15063, A-412997, FAUC-327, Ro-10-5824, CP-226269, PIP-3EA, FAUC-299, FAUC-316, FAUC-179, FAUC-356, FAUC-312, A-369509, and pharmaceutically acceptable salts thereof; more preferably one or more medicaments selected from the group consisting of PD-168077, ABT-724, ABT-670, F-15053, A-412997, FAUC-327, Ro-10-5824, CP-226269, PIP-3EA, and pharmaceutically acceptable salts thereof; and even more preferably one or more medicaments selected from the group consisting of PD-168077, ABT-724, ABT-670, F-15063, and pharmaceutically acceptable salts thereof.

Additional embodiment of the present invention is directed to a method for improving attention function in schizophrenia and/or bipolar disorder which comprises administering a therapeutically effective amount of lurasidone or a pharmaceutically acceptable acid addition salt thereof and a therapeutically effective amount of a $D_4$ receptor agonist to a mammal in need thereof.

Additional embodiment of the present invention is directed to a pharmaceutical product for treating ADHD which comprises lurasidone or a pharmaceutically acceptable acid addition salt thereof. In addition, the pharmaceutical product wherein treating ADHD is improving attention function in ADHD is also an embodiment of the present invention.

In addition, one embodiment of the invention is directed to a pharmaceutical product for treating ADHD which comprises lurasidone or a pharmaceutically acceptable acid addition salt thereof and a $D_4$ receptor agonist. In addition, the pharmaceutical product wherein treating ADHD is improving attention function in ADHD is also an embodiment of the present invention.

Additional embodiment of the present invention is directed to a kit for treating ADHD which comprises lurasidone or a pharmaceutically acceptable acid addition salt thereof. In addition, the kit wherein treating ADHD is improving attention function in ADHD is also an embodiment of the present invention.

In addition, one embodiment of the invention is directed to a kit for treating ADHD which comprises lurasidone or a pharmaceutically acceptable acid addition salt thereof and a $D_4$ receptor agonist. In addition, the kit wherein treating ADHD is improving attention function in ADHD is also an embodiment of the present invention.

Additional embodiment of the present invention is directed to use of lurasidone or a pharmaceutically acceptable acid addition salt thereof in the manufacture of a pharmaceutical composition for treating ADHD. In addition, the use wherein treating ADHD is improving attention function in ADHD is also an embodiment of the present invention.

In addition, one embodiment of the invention is directed to use of lurasidone or a pharmaceutically acceptable acid addition salt thereof and a $D_4$ receptor agonist in the manufacture of a pharmaceutical composition for treating ADHD. In addition, the use wherein treating ADHD is improving attention function in ADHD is also an embodiment of the present invention.

Additional embodiment of the present invention is directed to a pharmaceutical composition comprising lurasidone or a pharmaceutically acceptable acid addition salt thereof for use in the treatment of ADHD. In addition, the pharmaceutical composition wherein the treatment of ADHD is improvement of attention function in ADHD is also an embodiment of the present invention.

In addition, one embodiment of the invention is directed to a pharmaceutical composition comprising lurasidone or a pharmaceutically acceptable acid addition salt thereof and a $D_4$ receptor agonist for use in the treatment of ADHD. In addition, the pharmaceutical composition wherein the treatment of ADHD is improvement of attention function in ADHD is also an embodiment of the present invention.

Additional embodiment of the present invention is directed to use of lurasidone or a pharmaceutically acceptable acid addition salt thereof in the manufacture of a pharmaceutical composition for treating ADHD which is administered in combination with a $D_4$ receptor agonist. In addition, the use wherein treating ADHD is improving attention function in ADHD is also an embodiment of the present invention.

Additional embodiment of the present invention is directed to use of a $D_4$ receptor agonist for potentiating the efficacy of lurasidone or a pharmaceutically acceptable acid addition salt thereof for treating ADHD. In addition, the use wherein treating ADHD is improving attention function in ADHD is also an embodiment of the present invention.

Additional embodiment of the present invention is directed to use of lurasidone or a pharmaceutically acceptable acid addition salt thereof for potentiating the efficacy of a $D_4$ receptor agonist for treating ADHD. In addition, the use wherein treating ADHD is improving attention function in ADHD is also an embodiment of the present invention.

Additional embodiment of the present invention is directed to a medicament for treating ADHD which comprises lurasidone or a pharmaceutically acceptable acid addition salt thereof. In addition, the medicament wherein treating ADHD is improving attention function in ADHD is also an embodiment of the present invention.

In addition, one embodiment of the invention is directed to a medicament for treating ADHD which comprises lurasidone or a pharmaceutically acceptable acid addition salt thereof and a $D_4$ receptor agonist. In addition, the medicament wherein treating ADHD is improving attention function in ADHD is also an embodiment of the present invention.

In addition, one embodiment of the invention is directed to a medicament for treating ADHD which comprises lurasidone or a pharmaceutically acceptable acid addition salt thereof for the administration in combination with a $D_4$ receptor agonist. In addition, the medicament wherein treating ADHD is improving attention function in ADHD is also an embodiment of the present invention.

In addition, one embodiment of the invention is directed to a medicament for treating ADHD which comprises a $D_4$ receptor agonist for the administration in combination with lurasidone or a pharmaceutically acceptable acid addition salt thereof. In addition, the medicament wherein treating ADHD is improving attention function in ADHD is also an embodiment of the present invention.

The improvement of attention function in ADHD of the present invention includes improvement of attention deficit, hyperactivity disorder, etc., in more detail, improvement of impairment in a continuous concentration, improvement of a diminished rapid-reaction, improvement of a reduced activity, etc.

Preferably, the $D_4$ receptor agonist used herein includes, but is not limited thereto, the compounds listed in the following table and pharmaceutically acceptable acid addition salts thereof. More preferable $D_4$ receptor agonist includes PD-168077, ABT-724, ABT-670, F-15063, A-412997, FAUC-327, Ro-10-5824, CP-226269, PIP-3EA, and pharmaceutically acceptable acid addition salts thereof, and even more preferably, PD-168077, ABT-724, ABT-670, F-15063, and pharmaceutically acceptable acid addition salts.

The $D_4$ receptor agonist of the present invention may be used in a combination of two or more $D_4$ receptor agonists.

TABLE 1

| Drug Name [CAS Reg. No.] | Compound Name (Structure) | Reference |
|---|---|---|
| PD-168077 [190383-31-4] | N-[4-(2-Cyanophenyl)-piperazin-1-ylmethyl]-3-methylbenzamide | WO 2002041894 |
| ABT-724 [474417-17-9] | 2-[4-(2-Pyridyl)piperazin-1-ylmethyl)-1H-benzimidazole maleate | WO 2003/076431 WO 2002/088093 |
| ABT-670 | 3-Methyl-N-[4-(1-oxido-pyridin-2-yl)piperidin-1-ylmethyl]benzamide | WO 2003/099266 |
| F-15063 [680203-70-7] [680203-72-9 (fumarate)] | N-[3-(1-Cyclopenten-1-yl)benzyl]-N-[2-(2,2-dimethyl-2,3-dihydro-1-benzofuran-7-yloxy)ethyl]-amine | WO 2007/104872 WO 2004/035561 |

TABLE 1-continued

| Drug Name [CAS Reg. No.] | Compound Name (Structure) | Reference |
| --- | --- | --- |
| A-412997 [630116-49-3] | N-(3-Methylphenyl)-2-(4-(2-pyridyl)piperidin-1-yl)-acetamide | US 2003/229094 WO 2003/099266 |
| FAUC-327 | 3-[4-(4-Chlorophenyl)-piperazin-1-ylmethyl]-pyrazolo[1,5-a]pyridine-7-carbonitrile | Bioorganic & Medicinal Chemistry Letters 12 (2002) 633-636 |
| Ro-10-5824 [189744-46-5] | 2-Methyl-5-(4-phenyl-1,2,3,6-tetrahydropyridin-1-yl-methyl)pyrimidine-4-amine | WO 1997/013759 |
| CP-226269 | 5-Fluoro-2-(4-(2-pyridyl)-piperazin-1-ylmethyl)-1H-indole | US 2006/172995 US 7235661 |

TABLE 1-continued

| Drug Name [CAS Reg. No.] | Compound Name (Structure) | Reference |
|---|---|---|
| PIP-3EA | 2-[4-(2-Methoxyphenyl)-piperazin-1-ylmethyl]-imidazo[1,2-a]pyridine | J. Med. Chem. 2006, 49, 3938-3947 |
| FAUC-299 [313972-96-2] | 2-(4-Phenylpiperazin-1-yl-methyl)-1H-indole-5-carbonitrile | J. Med. Chem. 2000, 43, 4563-4569 |
| FAUC-316 [313973-04-5] | 2-[4-(4-Fluorophenyl)-piperazin-1-ylmethyl]-1H-indole-5-carbonitrile | J. Med. Chem. 2000, 43, 4563-4569 |
| FAUC-179 | 1-Phenyl-4-[2-phenyl-4,5-dihydro-1H-imidazol-4(R)-ylmethyl]piperazine hydrochloride | Bioorganic & Medicinal Chemistry Letters 11 (2001) 2533-2536 |
| FAUC-356 | 1-(4-Ethinyl-1H-pyrrol-2-yl-methyl)-4-phenylpiperazine | Bioorganic & Medicinal ChemistryLetters 12 (2002) 1937-1940 |

TABLE 1-continued

| Drug Name [CAS Reg. No.] | Compound Name (Structure) | Reference |
|---|---|---|
| FAUC-312 | 2-Phenyl-4(R)-(4-phenyl-piperazin-1-ylmethyl)-1,4,5,6-tetrahydropyrimidine 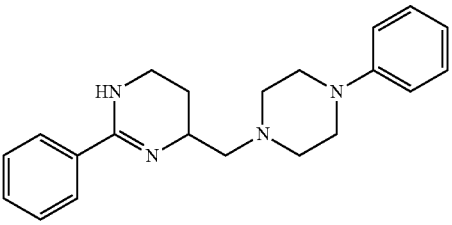 [SMILES: c1ccc(C2=NC(CN3CCN(c4ccccc4)CC3)CCN2)cc1] | Bioorganic & Medicinal Chemistry Letters 13 (2003) 851-854 |
| A-369508 | 2-[4-(2-Cyanophenyl)-piperazin-1-yl]-N-(3-methyl-phenyl)acetamide 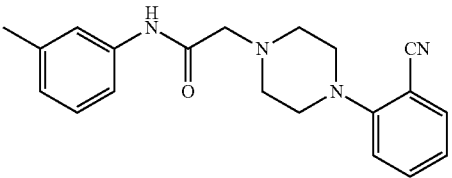 [SMILES: Cc1cccc(NC(=O)CN2CCN(c3ccccc3C#N)CC2)c1] | US 2003/229094 WO 2003/099266 |

Effect of the Invention

Lurasidone or a pharmaceutically acceptable acid addition salt thereof of the present invention is useful for treating ADHD, in particular, for improving attention function in ADHD. In addition, the effect of lurasidone or a pharmaceutically acceptable acid addition salt thereof can be enhanced by administering lurasidone or a pharmaceutically acceptable acid addition salt thereof in combination with a $D_4$ receptor agonist.

Further, the present invention can be also effective for improving a behavior disorder such as inhibition of aggression in ADHD; in more detail, effective for aggression against self and/or others, hostility, hyperactivity, severe impulsiveness, etc.

In addition, the present invention can be also effective for improving attention function in a patient suffering from schizophrenia and/or bipolar disorder.

BEST MODE FOR CARRYING OUT THE INVENTION

Figure 1:
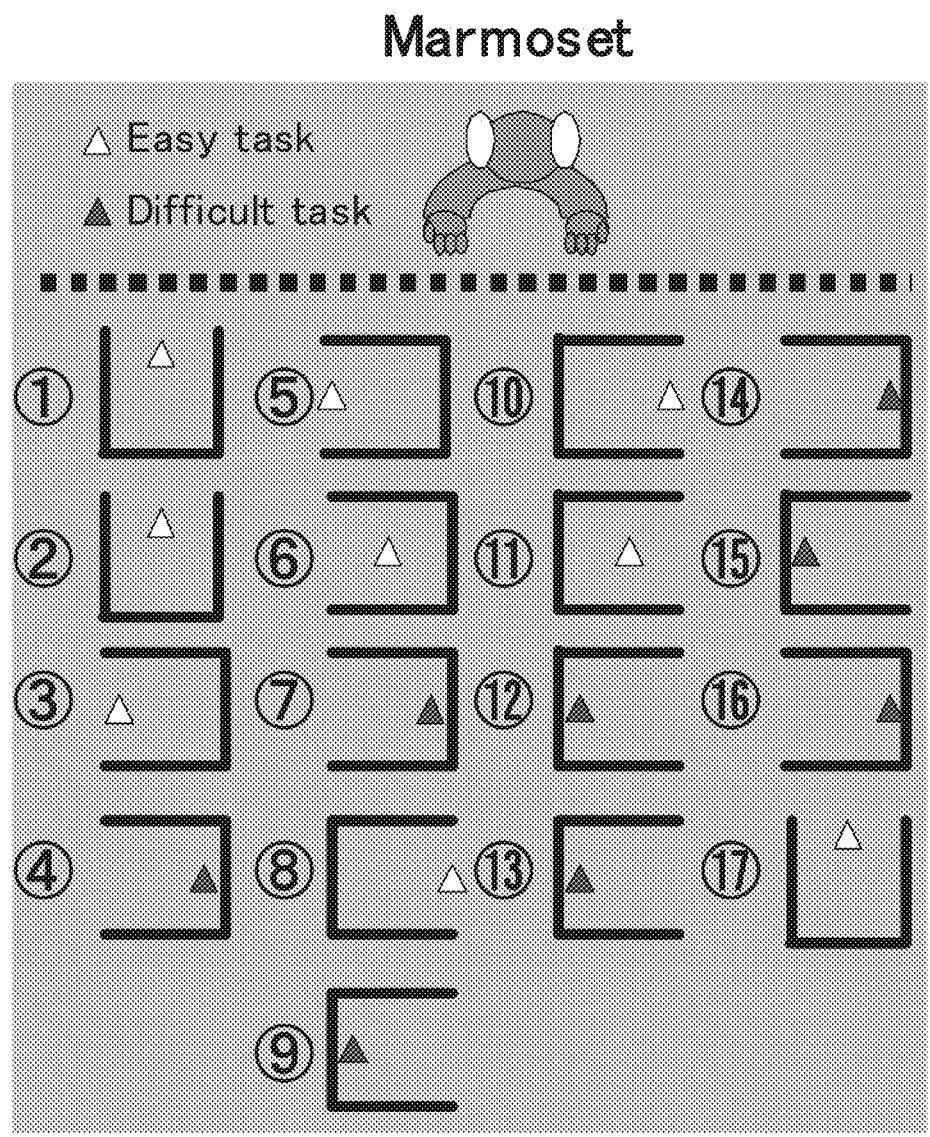
FIG. 1 depicts a marmoset, acryl boxes with a piece of Baumkuchen, a cage and the test pattern in EXAMPLE 1.
Figure 2:
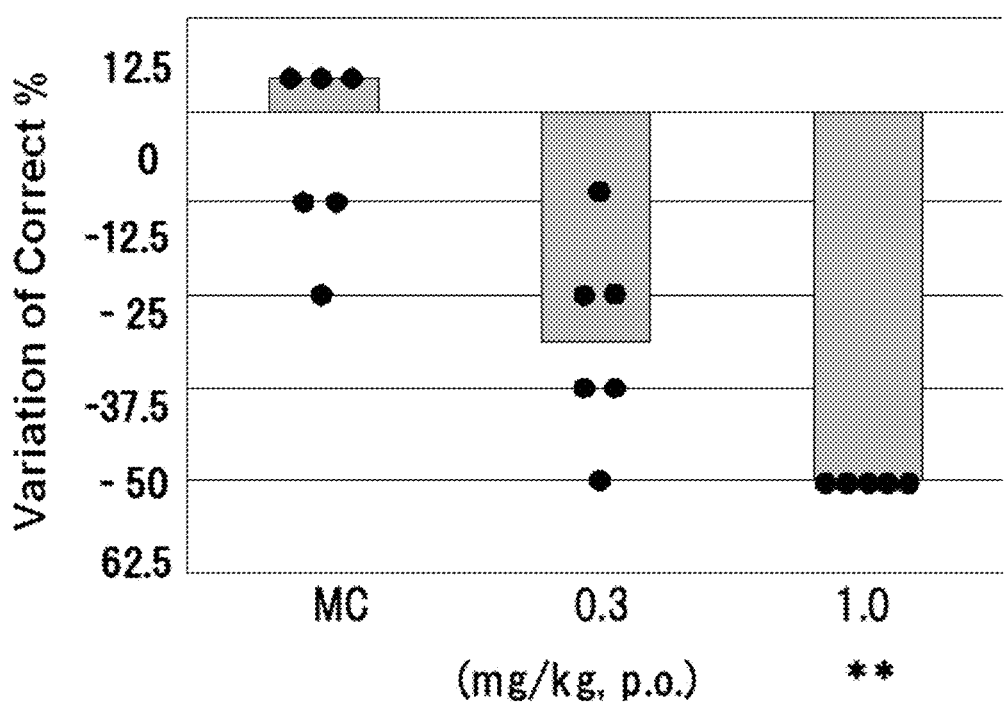
FIG. 2 shows the variation of the correct % between both results of the ORD test wherein one was carried out before the oral administration of haloperidol and the other was carried out 2 hours after the administration. The dot in the figure shows the variation of the correct % in each individual marmoset and the bar graph indicates the average value in each treated group.
Figure 3:
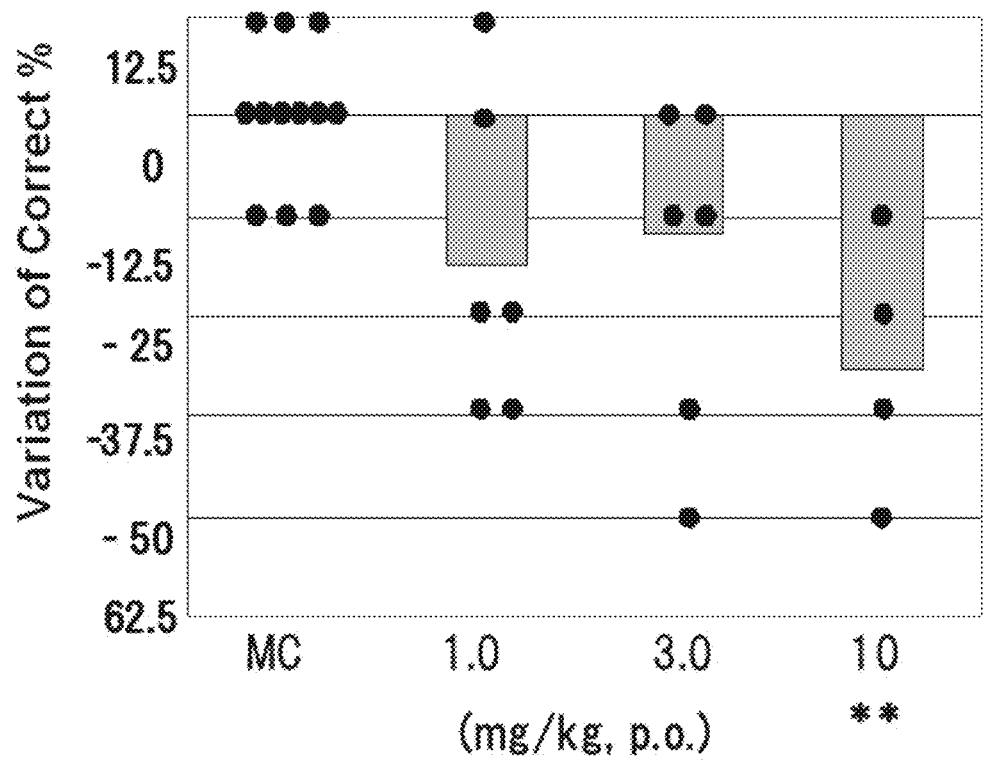
FIG. 3 shows the variation of the correct % between both results of the ORD test wherein one was carried out before the oral administration of clozapine and the other was carried out 2 hours after the administration. The dot in the figure shows the variation of the correct % in each individual marmoset and the bar graph indicates the average value in each treated group.
Figure 4:
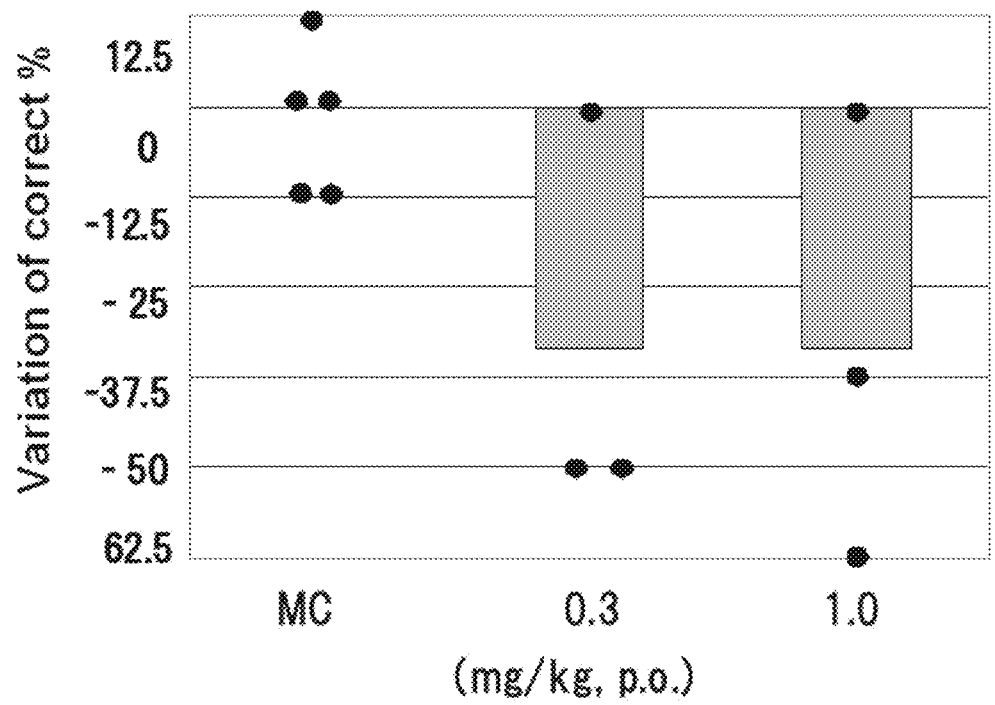
FIG. 4 shows the variation of the correct % between both results of the ORD test wherein one was carried out before the oral administration of risperidone and the other was carried out 2 hours after the administration. The dot in the figure shows the variation of the correct % in each individual marmoset and the bar graph indicates the average value in each treated group.
Figure 5:
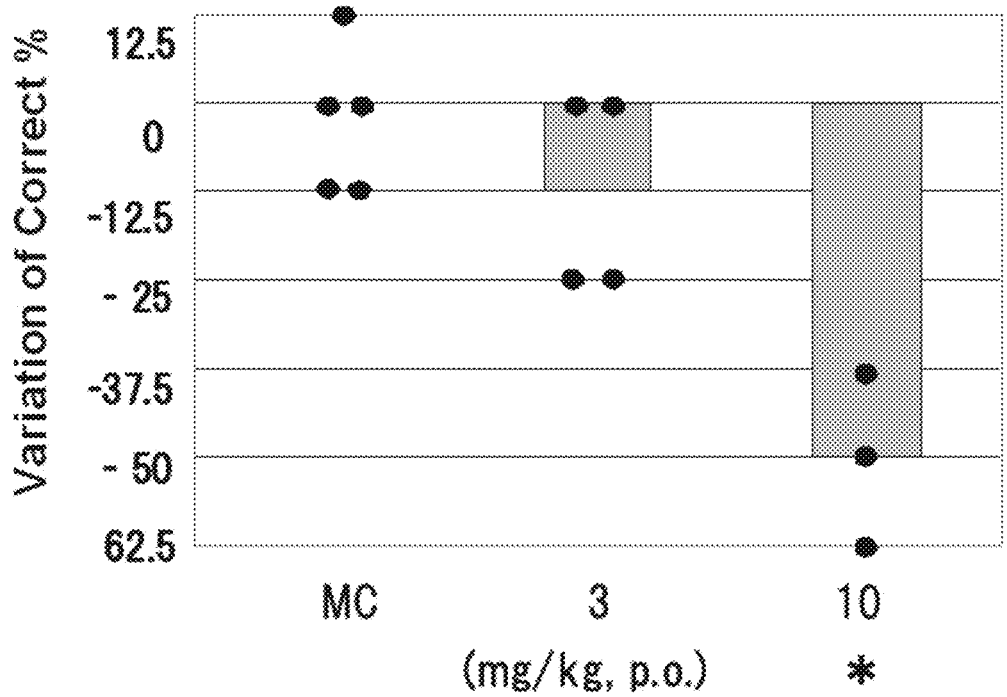
FIG. 5 shows the variation of the correct % between both results of the ORD test wherein one was carried out before the oral administration of olanzapine and the other was carried out 2 hours after the administration. The dot in the figure shows the variation of the correct % in each individual marmoset and the bar graph indicates the average value in each treated group.

Lurasidone may be used in form of the free base, optionally in form of its pharmaceutically acceptable acid addition salt and/or optionally in form of the hydrate and/or solvate thereof. Suitable acid addition salts include, for example, those of the acids selected from succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the above-mentioned acid addition salts may also be used. Amongst the aforementioned acid addition salts, the hydrochloride and the hydrobromide, particularly the hydrochloride, are preferred.

The present invention includes prodrugs of lurasidone or a pharmaceutically acceptable acid addition salt thereof and a $D_4$ receptor agonist. In general, such prodrugs are functional derivatives of the compounds of this invention which are readily convertible in vive into the required compound.

The exemplified prodrugs of the invention, but are not limited to, include the following types:

Phosphate ester prodrug for hydroxyl or amine group of the parent drug.

Carbonate or carbamate prodrug for carboxyl, hydroxyl or amine group of the parent drug.

Amide prodrug for carboxylic acid or amine group of the parent drug.

Amino acid-attached prodrug for carboxylic acid or amine group of the parent drug.

Oxime prodrug for ketone, amidine or guanidine group of the parent drug.

The prodrugs of the invention can be prepared, for example, by means disclosed in *Nature Reviews Drug Discovery* 7; 255-270 (2008); or *Journal of Medicinal Chemistry* 2005, 48 (16), 5305-5320.

The term "therapeutically effective amount" shall mean the amount of a drug or pharmaceutical agent that will elicit the biological or medical response of a tissue, system, animal or human that is being sought by a researcher or clinician.

The terms "treating" and "treatment" used herein include any treatment of the disease (e.g. improvement of the symptoms, relief of the symptoms, arrest of the development of the symptoms, etc.) as well as any prevention of the disease (e.g. prevention of the onset and/or progression of the disease).

As used herein, the term "pharmaceutical product" is intended to encompass a product comprising the specified ingredients in the specified amounts, as well as any product which results, directly or indirectly, from combination of the specified ingredients in the specified amounts.

The term "ADHD" used herein means attention deficit/hyperactivity disorder, in more detail, one of developmental disorders, which is characterized by inattention, hyperactivity, and impulsiveness. The symptom includes difficulty in concentrating, overactivity, and inattention.

In addition, the improvement of ADHD includes inhibition of aggression, and the specific behavior disorder of aggression includes aggression against self and/or others, hostility, hyperactivity, severe impulsiveness, etc.

The improvement of impairment in a continuous concentration, the improvement of a diminished rapid-reaction, and the improvement of a reduced activity, which are examples of the improvement of attention function in ADHD of the present invention, can be evaluated by visual/perceptual seeking and/or systematic/continuous listening as a marker of the improvement.

In the combination of the present invention, lurasidone or a pharmaceutically acceptable acid addition salt thereof and a $D_4$ receptor agonist may be administered separately or together in one pharmaceutical composition. In addition, the administration of one element of the combination of the present invention may be prior to, concurrent with, or subsequent to the administration of the other element of the combination. These ingredients may be formulated into a single dosage form or two separate ones.

Lurasidone and a $D_4$ receptor agonist of the present invention can be easily reacted with a pharmaceutically acceptable acid to form a salt thereof. The acid includes an inorganic acid such as hydrochloric acid, sulphuric acid, phosphoric acid, and hydrobromic acid; and an organic acid such as oxalic acid, maleic acid, fumaric acid, malic acid, tartaric acid, citric acid, and benzoic acid. A preferable salt of lurasidone includes the hydrochloride thereof.

The active ingredients of the present invention (lurasidone or a pharmaceutically acceptable acid addition salt thereof, or the combination of lurasidone or a pharmaceutically acceptable acid addition salt thereof and a $D_4$ receptor agonist) may be administered by oral, parenteral (e.g., intramuscular, intraperitoneal, intravenous or subcutaneous injection, or implant), buccal, nasal, vaginal, rectal, sublingual, or topical (e.g., ocular eyedrop) routes of administration and may be formulated alone or together, in suitable dosage unit formulations containing conventional non-toxic pharmaceutically acceptable carriers, adjuvants and vehicles appropriate for each route of administration.

Lurasidone and a pharmaceutically acceptable acid addition salt thereof of the present active compound can be orally administered in a needed amount suitable for the active ingredient, as a generally-used dosage form such as tablet, capsules, syrup, and suspension, or parenterally administered as an injection form such as solution, emulsion, suspension and patch.

The above-mentioned drug form can be prepared by formulating the active compound with conventional additives such as carrier excipient, binder, and stabilizer. In the case of injections, for example, acceptable buffer, solubilizer, isotonic agent and pH adjuster can be also used.

The dosage of the active ingredients of the present invention is not limited, but it can vary depending upon dosage amount of each active ingredient, frequency of administration, administration form, condition of a patient suffering from the disease. For example, lurasidone or a pharmaceutically acceptable acid addition salt thereof of the present invention can be orally administered in a dosage of 1-200 mg, preferably 20-160 mg, per day for an adult, and once to several times a day. The $D_4$ receptor agonist can be orally administered in a dosage of 1-600 mg per day for an adult, and once to several times a day.

When these active ingredients are prepared in a single dosage form, the $D_4$ receptor agonist is generally contained in 0.1 to 10 parts, preferably 0.3 to 3 parts, by weight per one part by weight of lurasidone or a pharmaceutically acceptable acid addition salt thereof. And, the drug combination may include the sum of the ingredients in 0.1-70% (w/w) in the preparation, but not limited thereto.

EXAMPLE

Hereinafter, the present invention is further illustrated by Examples, but should not be construed to be limited thereto.

Example 1

(Method)

ORD test (object retrieval with detour test) is already reported as a method for evaluating executive function (attention function/impulsiveness) in primates. The present inventors have found that the method is useful as a model experiment for evaluating ADHD, then carried out the following test according to the method.

Male and female common marmosets having body weights of 250-450 g were used. Haloperidol, clozapine, olanzapine, risperidone, and lurasidone hydrochloride were separately suspended in 0.5% methylcellulose (MC), and then each suspension was orally administered in a dose of 5 mL/kg to the marmosets. On the other hand, L-745,870 which is a $D_4$ antagonist, and Ro 10-5824 which is a $D_4$ agonist were separately dissolved in saline, and then each solution was intramuscularly administered to the femoris area in a dose of 0.5 mL/kg.

According to the method described in the literature (*Psychopharmacology* (2008) 196: 643-648) which was partially modified, the ORD test was carried out as follows (see FIG. 1).

(Training for ORD Test)

Clear acrylic cubic boxes (dimensions: 4 cm×4 cm×4 cm) with one open side are set as the thick frames shown in FIG. 1. In each of the boxes, 0.3-0.5 g of Baumkuchen as a food reward is placed at the point of each triangle in FIG. 1. The marmoset can reach out from the cage (shown as dotted line region) to obtain the reward placed in the acrylic box. FIG. 1 is a view from the directly above. Amongst the situations between each direction of the box and each position of the reward, 5 patterns (line of sight, left outside, left inside, right outside, and right inside) are defined as "easy task", and the other 2 patterns (left deep, and right deep) are defined as "difficult task". It is recorded as "correct" when the test animal can obtain the reward in one trial, while it is recorded as "incorrect" when the animal can obtain the reward in the second trial or later.

The ORD test is carried out in the order described in the following table without any interval between each trial, which is referred to as "one series". The marmoset is made to be trained with the one series once a day.

TABLE 2

| Trial number | Position of the reward | Level |
|---|---|---|
| 1 | Line of sight | Easy |
| 2 | Line of sight | Easy |
| 3 | Right outside | Easy |
| 4 | Right deep | Difficult |
| 5 | Right outside | Easy |
| 6 | Right inside | Easy |
| 7 | Right deep | Difficult |
| 8 | Left outside | Easy |
| 9 | Left deep | Difficult |
| 10 | Left outside | Easy |
| 11 | Left inside | Easy |
| 12 | Left deep | Difficult |
| 13 | Left deep | Difficult |
| 14 | Right deep | Difficult |
| 15 | Left deep | Difficult |
| 16 | Right deep | Difficult |
| 17 | Line of sight | Easy |

The marmosets were trained with the ORD test at least 10 times, and then the trained marmosets were used in the following main test.

The main ORD test was carried out as follows.

(1) The ORD test is carried out before administering each test drug (former value). Hereinafter, the ORD test is done in one series containing the 17 trials corresponding to the above-mentioned training.

(2) Two hours after administering each test drug, the same ORD test is carried out again (latter value). In case of the combined administration, the first drug (lurasidone hydrochloride) is administered; one hour later, the second drug (the $D_4$ antagonist or $D_4$ agonist) is administered; and then the ORD test is done one hour after the second drug is administered.

(3) The variation of correct % in the Difficult task is calculated according to the following formula in order to evaluate the effect of each drug. For example, in case that the "correct count" in the before-administration test (former value) is 3 and the "correct count" in the after-administration test (latter value) is 5, the "correct %" is calculated to rise in 25% (=(5−3)/8×100%) based on the fact that the trial count of the difficult task in each series is 8.

The variation of the correct %={the difference between the both correct counts in the difficult task (latter value−former value)}/8×100

(4) The amount of Baumkuchen is 0.5 g×17=8.5 g in one series. The marmoset can be tested at most 2 sets per day, i.e. it has been confirmed that the marmoset can take at most 17 g of Baumkuchen per day, but, all the test marmosets cannot be satisfied with 17 g of Baumkuchen.

(5) In case that a marmoset treated with the drug is used again, the marmoset is given in 2 week-drug-holidays, and before the test it is confirmed that the previous medication will not affect the test.

(6) 5 to 6 marmosets were used per one test group. When a marmoset (s) suffered from vomiting or cataleptic akinesia induced by the drug and then the ORD test with the marmoset(s) could not be done, the data of the marmoset(s) were excluded. And, when the test for one drug is done over 2 days, the solvent test (control group) is done in both the days. Thereby, in some cases, the control group can include the data using at most 12 animals (6 animals×2 times).

(Result 1)

Figure 6:
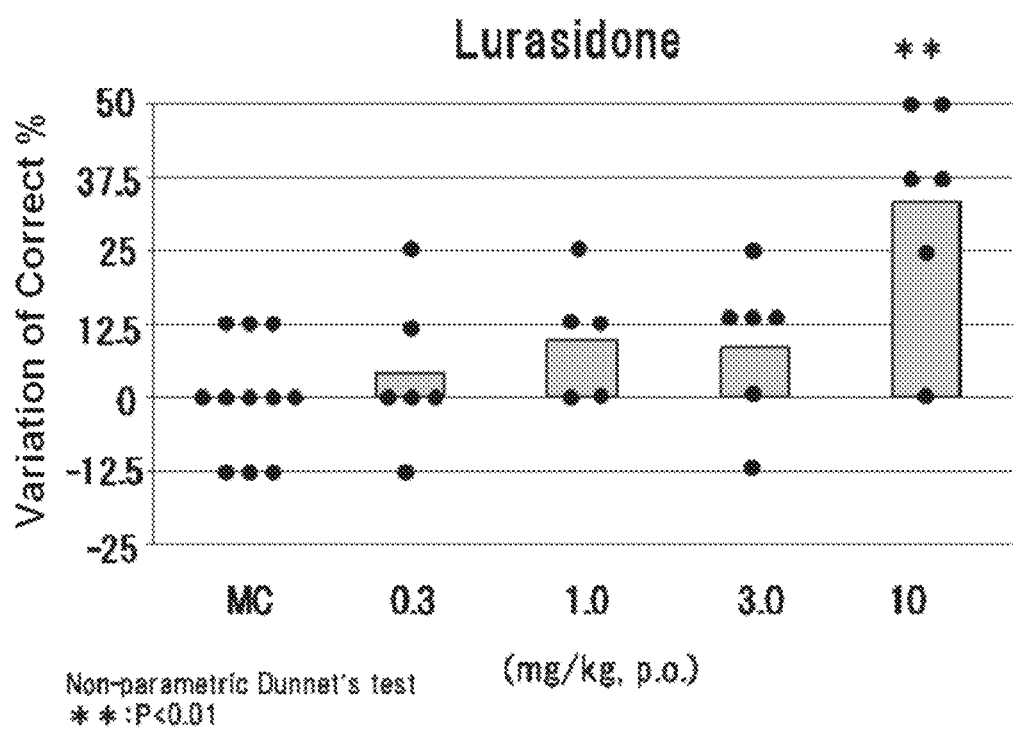
FIG. 6 shows the variation of the correct % between both results of the ORD test wherein one was carried out before the oral administration of lurasidone hydrochloride and the other was carried out 2 hours after the administration. The dot in the figure shows the variation of the correct % in each individual marmoset and the bar graph indicates the average value in each treated group. Note that "Lurasidone (mg/kg, p.o.)" shown in FIG. 6-8 means the dose of lurasidone hydrochloride.

As shown in FIG. 2 to 5, haloperidol, clozapine, risperidone and olanzapine in each single administration decreased the correct % of the ORD test in a dose-dependent manner. On the other hand, lurasidone hydrochloride increased the correct % of the ORD test in a dose-dependent manner as shown in FIG. 6. Namely, it was indicated that lurasidone hydrochloride in single administration can improve attention function in ADHD and suppress impulsiveness.

(Result 2)

Figure 7:
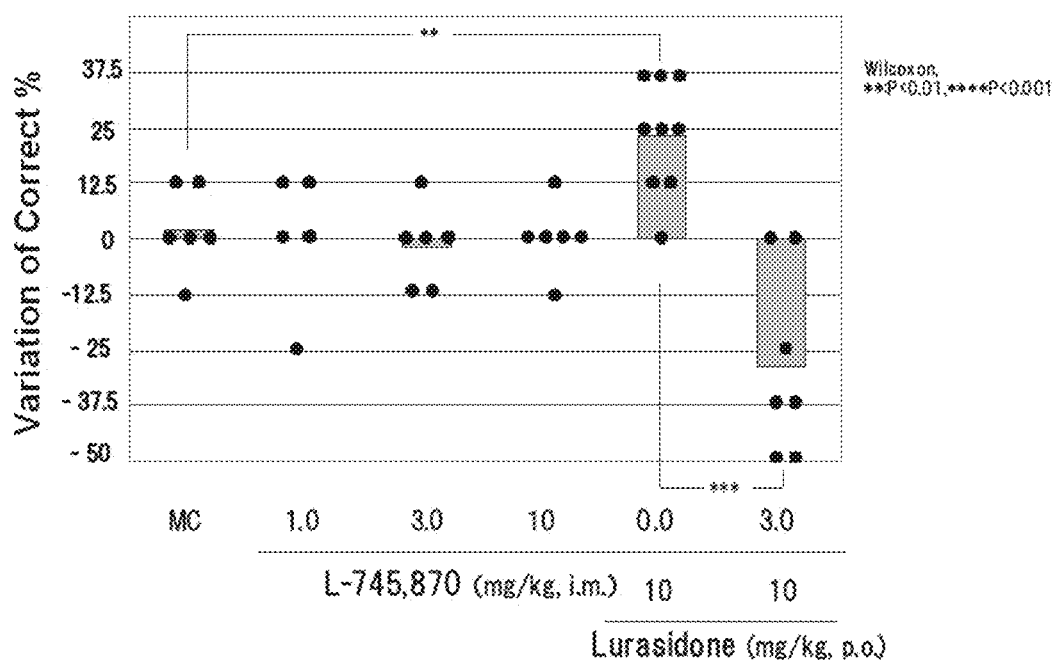
FIG. 7 shows the variation of the correct % in single administration of L-745,870 or in the combined administration with lurasidone hydrochloride (10 mg/kg, p.o.). The dot in the figure shows the variation of the correct % in each individual marmoset and the bar graph indicates the average value in each treated group.

Although the single intramuscular administration of L-745,870 which is a $D_4$ antagonist (10 mg/kg) had no effects on the ORD score as shown in FIG. 7, the combined administration of L-745,870 (3 mg/kg, i.m.) with lurasidone hydrochloride (10 mg/kg, p.o.) decreased the correct % which was increased by the administration of lurasidone hydrochloride. It seems that lurasidone failed to decrease the ORD score because of its weak $D_4$ antagonistic actions in contrast to the strong $D_4/D_2$ receptor antagonistic actions of SDAs (serotonin dopamine antagonists) other than lurasidone.

(Result 3)

Figure 8:
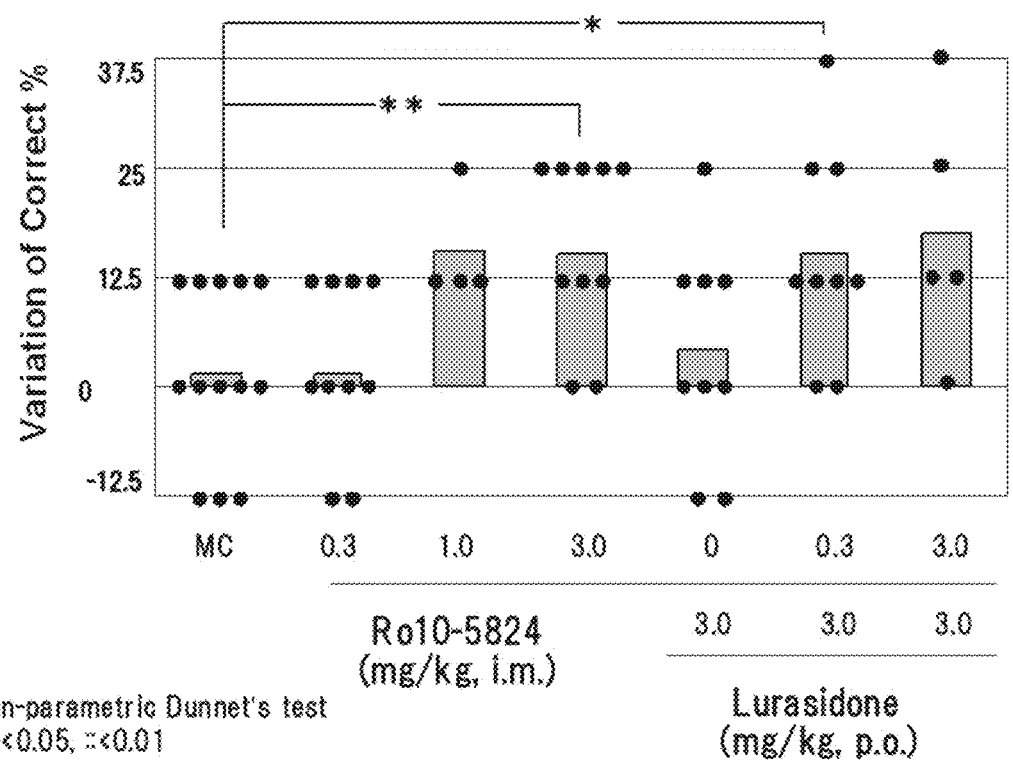
FIG. 8 shows the variation of the correct % in single administration of Ro 10-5824 or in the combined administration with lurasidone hydrochloride (3 mg/kg, p.o.). The dot in the figure shows the variation of the correct % in each individual marmoset and the bar graph indicates the average value in each treated group.

As shown in FIG. 8, the single administration of Ro 10-5824 which is a $D_4$ agonist increased the ORD score in a dose dependent manner. Also, when the administration of lurasidone hydrochloride (3 mg/kg, p.o.) which had no effects on the correct % was combined with the administration of Ro 10-5824 (003 mg/kg, i.m.) which is also had no effects on the correct %, the ORD score was significantly increased. These results suggest that the application of lurasidone as a combination drug with $D_4$ agonist could enhance the therapeutic effects in ADHD therapy. Also, these results suggest a possibility that a compound having both SDA action and $D_4$ agonist action could be a medicament for treating ADHD. Among deficits in attention function which are the symptoms of ADHD, in particular, such medication is expected to improve continuous concentration, rapid-reaction and visual/perceptual seeking.

Example 2

According to the five-choice serial reaction time task test (5-CSRT test) which is based on the procedure described in *Neuropharmacology*, 2006 August; 51(2): 238-50. Epub 2006 May 6. or *Brain Res Cogn Brain Res*. 2004 April; 19(2): 123-3, it is possible to evaluate the effect of the compounds or the combination drugs of the present invention for improving deficits in attention function which are the symptoms of ADHD, in particular, continuous concentration, rapid-reaction and visual/perceptual seeking.
(Animals)
Common marmosets (male/female, 250-450 g weight) are used.
(Induction of Cognitive Impairment)
Transient cognitive impairment is induced in the marmosets by the intramuscular administration of ketamine hydrochloride (1.0-3.0 mg/kg). 15 min after the administration, the 5-CSRT test is initiated.
(Drugs, Preparation and Administration Methods)
A suspension of 0.5% lurasidone hydrochloride in methylcelluose (MC) is orally administrated to the marmosets (0.1-30 mg/kg). On the other hand, L-745,870 which is a $D_4$ antagonist and Ro 10-5824 which is a $D_4$ agonist are dissolved in saline, and intramuscularly administrated to the femoris area in a dose of 0.1-10 mg/kg and 0.1-3 mg/kg, respectively. These drugs are administrated 1-2 hours prior to the ketamine administration.
(5-CSRT Test)
The 5-CSRT test is performed according to the following procedure which is made by partially modifying that of the above reference (*Neuropharmacology*. 2006 August; 51(2): 238-50. Epub 2006 May 6.).
A system called CANTAB (Cambridge Neuropsychological Test Automated Battery) in which computerized tasks can be presented on a personal computer and a food reward is given for a correct answer, is employed. A piece of Baumkuchen (0.1-0.3 g) is given to each individual through the CNTAB device as a food reward for the correct answer. The marmosets reach out from the cage, answer the tasks provided by CANTAB device, and make actions to obtain the food reward.
In the tasks of the 5-CSRT test, white lined circles having a diameter of 3 cm are presented at each vertex of an equilateral pentagon of 10 cm on a side, and only one of the 5 circles is lighted to yellow inside the white line for a period of 0.2 to 1.0 sec, then the yellow signal is blacked out. And, the marmosets can touch the lighting circle, and will be given the reward for the correct answer if they touch the lighting circle in the lighting period or within 15 sec after the extinction. Each task is loaded in every 5 sec, and the numbers of correct answers, wrong answers and omission, and time to respond to the task are recorded to evaluate the effect of drugs. The tasks consist of up to 30 tasks and up to 10 min of the total test period.

Example 3

Suitably designed clinical tests for evaluating deficits in attention function in ADHD include Continuous Performance Test (CPT) (Reference URL1), Test of Variables of Attention (T.O.V.A) (Reference URL2). Alternatively, the improvement of deficits in attention function in ADHD by the compound and the combination drug of the present invention can be confirmed using NIH Test of Attention (Reference URL2) operated in NIDCD (National institute on deafness and other communication disorders) of the NIH (National institute of health) and a clinical test based on new CPT (Reference URL3) which is a modified CPT test,
Reference URL1
ClinicalTrials.gov Identifier: NCT00546910
http://clinicaltrials.gov/ct2/show/NCT00546910
Reference URL2
ClinicalTrials.gov Identifier NCT00776737
http://clinicaltrials.gov/ct2/show/NCT00776737
Reference URL3
ClinicalTrials.gov Identifier: NCT00616464
http://clinicaltrials.gov/ct2/show/NCT00646464

Example 4

The improvement of deficits in attention function in ADHD by the compound and the combination drug of the present invention can be confirmed using clinical tests based on the procedures described in Reference 1 and Reference 2 as suitably designed clinical test for evaluating deficits in attention function in ADHD.
Reference 1: *Rinsho Seishin Yakuri*, vol. 12, issue. 9, Page 1957-1964 (2009 September)
Reference 2: *Rinsho Seishin Yakuri*, Vol. 12, issue 9, Page 1965-1977 (2009 September)
Specifically, for example, by comparing the total score of ADHD RS-IV (ADHD Rating Scale-IV, Japanese edition (clinician version)) before and after the administration of the compound or combination drug of the present invention for a certain period (e.g., but not limited to, 8 weeks) to 6 to 18 years old patients fulfilling the diagnostic criteria of ADHD based on DSM-IV (*Diagnostic and Statistical Manual of Mental Disorders*, 4th. Edition), the improvement of deficits in attention function which are the symptoms of ADHD can be confirmed (Reference 1, Page 1958-1960).
In the tests described above, conditions such as patients, administration period, dose, and methods for assessment can be appropriately modified. For example, evaluation according to scores of Inattention Subscale of ADHD RS-IV consisting of 9 terms, evaluation according to scores of Hyperactivity-Impulsiveness Subscale consisting of 9 terms, and/or evaluation according to ADHD generalized severity (CGI-ADHD-S) can be employed besides the total scores of ADHD RS-IV. Furthermore, other tests described in Reference 1 and Reference 2, and tests described in reference literatures in these References as well as tests with appropriately modificated conditions of above tests can also be employed.

Example 5

According to the Y-maze test with juvenile stroke-prone spontaneously hypertensive rats (SHRSP), it is possible to evaluate the effect of lurasidone hydrochloride on attention function with spontaneous Alternation Behavior as an index of attention or concentration (Behav Brain Funct. 2005 Jul. 15; 1:9). Moreover, the effects of lurasidone hydrochloride on hyperactivity, which is one of core symptoms in ADHD, can be confirmed by the total number of the Arm Entries in a Y-maze test.

(Y-Maze Test with SHRSP Rats)

Methods:

For the estimation of inattentive behavior, male juvenile SHRSP rats as an ADHD model and WKY rats as a reference (4 weeks old, n=8-10/group) are used. These animals are commercially available from Charles River Laboratories Japan, inc. or Hoshino Laboratory animals, inc. Lurasidone hydrochloride (e.g. 0.01, 0.03, 0.1, 0.3, 1, 3 and 10 mg/kg; produced by Dainippon Sumitomo Pharma Co., Ltd.) is dissolved in 0.5% methylcellulose and 0.2% Tween 80, and is administrated intraperitoneally in a volume of 1 ml/kg, 30 minutes before the evaluation.

The method of Y-maze test was already reported elsewhere (Behav Pharmacol. 2002 February; 13(1):1-13). The "Arm Entry" means the entry of all four paws into one arm. The "Alternation Behavior", which is actual alternations, means the consecutive Arm Entries into three different arms. The test is carried out for 8 minutes in one session and the total number that a rat performs the Arm Entry is counted. The "Maximum Alternations" means the total number of the Arm Entries minus two. An index of attention is calculated as a percentage of the Alternation Behavior, as described below.

A percentage of Alternation Behavior=(the total number of the Alternation Behavior)/(the Maximum Alternations)×100

Results:

The increased number of total Arm Entries and the decreased percentage of Alternation Behavior were observed in the SHRSP rats compared to the WKY rats, indicating hyperactivity and inattention behavior in the SHRSP, respectively. After the administration of 0.1, 0.3 or 1.0 mg/kg of lurasidone hydrochloride, the Alternation Behavior was improved in the SHRSP rats, with a statistical significance at 0.3 (p=0.0124) mg/kg. Furthermore the SHRSP to which lurasidone hydrochloride was given in a dose of 0.1, 0.3 or 1.0 mg/kg showed the decreased number of total Arm Entries with a statistical significance at 0.3 (p=0.0096) and 1 (p=0.0047) mg/kg, suggesting attenuated hyperactivity in the SHRSP. Thus, it is concluded that lurasidone hydrochloride improved inattention behavior and hyperactivity in SHRSP.

TABLE 3

| | Inattention | |
|---|---|---|
| Animal species | Dose (mg/kg) | % of Alternation Behavior mean ± SE |
| WKY | 0 | 82 ± 3 |
| SHRSP | 0 | 61 ± 2 |
| SHRSP | 0.1 | 70 ± 5 |
| SHRSP | 0.3 | 75 ± 2 * |
| SHRSP | 1.0 | 72 ± 2 |

*: $p < 0.05$

TABLE 4

| | Hyperactivity | |
|---|---|---|
| Animal species | Dose (mg/kg) | Total Arm Entries mean ± SE |
| WKY | 0 | 20 ± 1 |
| SHRSP | 0 | 27 ± 1 |
| SHRSP | 0.1 | 24 ± 1 |
| SHRSP | 0.3 | 22 ± 2 * |
| SHRSP | 1.0 | 21 ± 1 * |

*: $p < 0.05$

Example 6

The elevated-plus maze with SHRSP makes it possible to estimate the effects of lurasidone hydrochloride on impulsivity, which is one of main symptoms of ADHD (Behav Brain Funct. 2005 Jul. 15; 1:9). In particular, it is possible to confirm the effect of lurasidone hydrochloride on impulsivity by measuring the spending time on open arms and/or the number of the entry into open arm in an elevated-plus maze. WKY rats are available as a normal animal.

(Elevated Plus Maze in SHRSP Rats)

Methods

The spending time on open arms in an elevated plus maze can be used as an index of impulsive-like behavior according to the method described previously (Behav Pharmacol. 2002 February; 13(1):1-13). For the estimation of impulsivity, male juvenile SHRSP rats as an ADHD model and WKY rats as a reference (5 weeks old, n=8-10/group) are used. These animals are commercially available from Charles River Laboratories Japan, inc. or Hoshino Laboratory animals, inc. Lurasidone hydrochloride (e.g. 0.01, 0.03, 0.1, 0.3, 1, 3 and 10 mg/kg; produced by Dainippon Sumitomo Pharma Co., Ltd.) is dissolved in 0.5% methylcellulose and 0.2% Tween 80, and is administrated intraperitoneally in a volume of 1 ml/kg, 30 minutes before the evaluation. A plus maze with two open and close arms (50 cm×10 cm) is elevated 50 cm above a floor. After the administration of lurasidone hydrochloride, SHRSP or WKY rat is placed in the center area and allowed to enter each arm freely for a 10 min session. Analysis is performed with a video tracking software, EthoVision@XT (Noldus Information Technology), in which the "Arm Entry" means an entry of a body center.

There is no significant difference in the spending time on closed arms between SHRSP and WKY, while SHRSP spends for a longer time on open arms. They indicate impulsive behavior and/or less anxiety in SHRSP. The decrease of time which SHRSP spends on open arms of an elevated-plus maze indicates the improvement of impulsivity by the compound. Thus, the ameliorating effect of lurasidone hydrochloride on impulsivity can be evaluated.

The invention claimed is:

1. A method for improving behavior disorder, comprising: administering a pharmaceutical composition comprising, as a sole active ingredient, a therapeutically effective amount of lurasidone or a pharmaceutically acceptable acid addition salt thereof to a mammal in need thereof, wherein the behavior disorder is one or more disorders selected from the group consisting of hyperactivity and severe impulsiveness.

2. The method of claim 1, wherein the pharmaceutical composition is a tablet comprising lurasidone hydrochloride as the sole active ingredient, and the tablet is orally administered at a dosage of 20 mg to 160 mg per day.

3. The method of claim 1, wherein the behavior disorder is hyperactivity in schizophrenia.

4. The method of claim 1, wherein the behavior disorder is severe impulsiveness in schizophrenia.

5. The method of claim 1, wherein the behavior disorder is hyperactivity in bipolar disorder.

6. The method of claim 2, wherein the behavior disorder is hyperactivity in schizophrenia.

7. The method of claim 2, wherein the behavior disorder is severe impulsiveness in schizophrenia.

8. The method of claim 2, wherein the behavior disorder is hyperactivity in bipolar disorder.

* * * * *